United States Patent [19]

Summer

[11] Patent Number: 4,969,822
[45] Date of Patent: Nov. 13, 1990

[54] ORAL ORTHOPEDIC APPLIANCE FOR CORRECTING MANDIBULAR RETRUSION

[76] Inventor: John D. Summer, 1427 NW. 23rd St., Portland, Oreg. 97210

[21] Appl. No.: 263,087

[22] Filed: Oct. 27, 1988

[51] Int. Cl.⁵ .............................................. A61C 3/00
[52] U.S. Cl. .................................................... 433/19
[58] Field of Search ....................... 433/17, 19, 18, 21, 433/22

[56] References Cited

U.S. PATENT DOCUMENTS

| | | | |
|---|---|---|---|
| 3,618,214 | 11/1971 | Armstrong | 433/19 |
| 4,382,782 | 5/1983 | Klein et al. | 433/18 |
| 4,382,783 | 5/1983 | Rosenberg | 433/19 |
| 4,416,627 | 11/1983 | Beazley | 433/17 |
| 4,424,032 | 1/1984 | Howe | 433/19 |
| 4,462,800 | 7/1984 | Jones | 433/19 |
| 4,472,138 | 9/1984 | Howe | 433/19 |
| 4,618,324 | 10/1986 | Nord | 433/19 |
| 4,795,342 | 1/1989 | Jones | 433/19 |

FOREIGN PATENT DOCUMENTS 374163  7/1921  Fed. Rep. of Germany .
1079955 12/1954  France .

*Primary Examiner*—Cary E. Stone
*Attorney, Agent, or Firm*—Klarquist, Sparkman, Campbell Leigh & Whinston

[57] ABSTRACT

A telescopic oral orthopedic appliance aligns the upper and lower jaws for treatment of the temporomandibular joint. It includes an extensible-contractable positioning device which extends between and alters the position of the mandible relative to the maxillae. The device is attached to upper and lower sets of teeth by an anchor which is embedded in a pair of opposing channel members which fit over the apex and inwardly and outwardly facing walls of the clinical crowns of a series of adjacent teeth. The extensible-contractable device fits closely against the channel member to avoid rubbing the buccal mucosa of the wearer's mouth. The length of the device is selectively variable to alter the position of the mandible forward or backward without sudden jumps or the need for removing the appliance from the mouth.

37 Claims, 1 Drawing Sheet

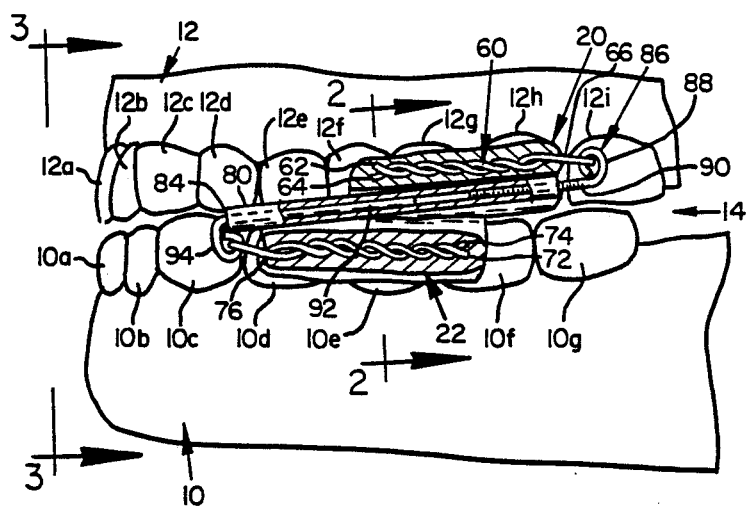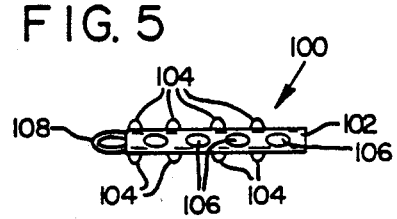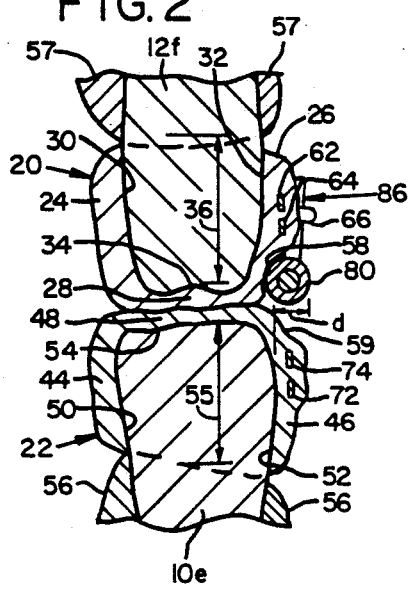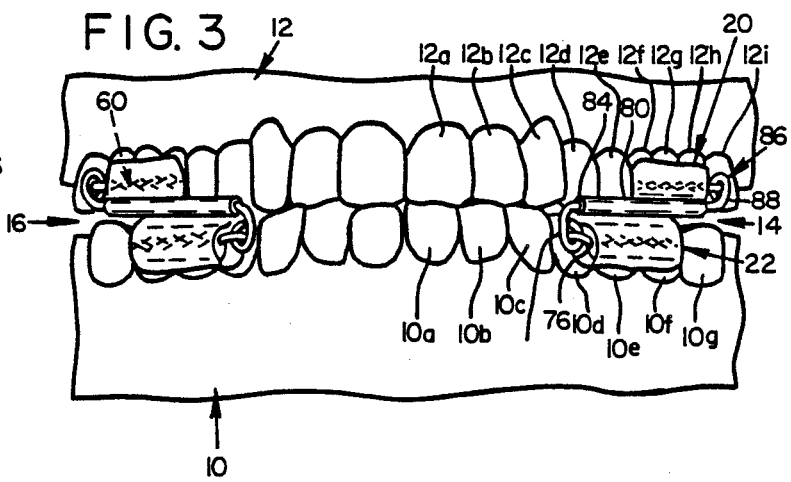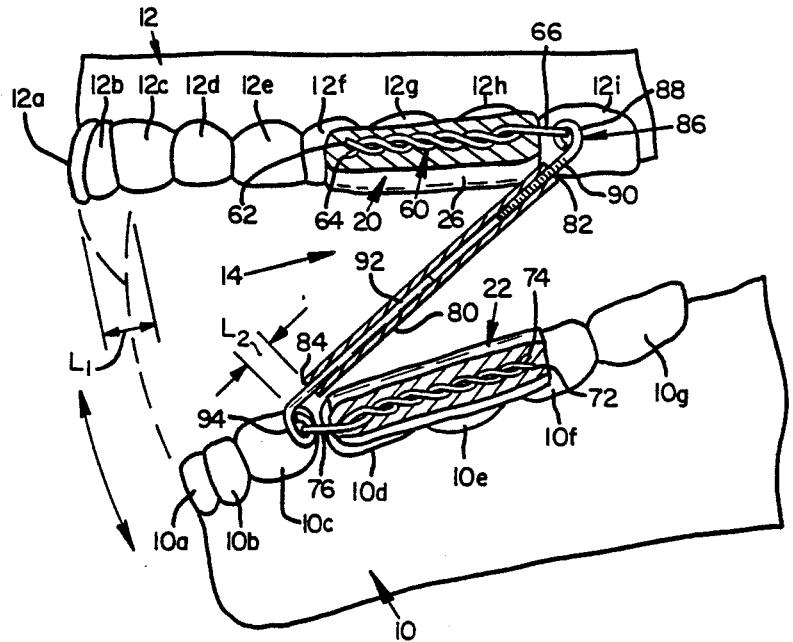

ORAL ORTHOPEDIC APPLIANCE FOR CORRECTING MANDIBULAR RETRUSION

BACKGROUND OF THE INVENTION

1. Field of the Invention

The present invention relates to an intraoral orthopedic appliance to align the mandible and maxilla for treatment of temporomandibular joint disorders.

2. General Discussion of the Background

Mandibular retrognathia is a common cause of temporomandibular joint disorders. In this condition, a misalignment of the mandible and maxilla forces the mandible backwards into the temporomandibular joint and causes a mechanical strain which can result in dislocation of the joint or degeneration of the muscles protecting the joint. Other symptoms include tenderness in the muscles of mastication, jaw opening limitation, clicking or popping sounds in the joint, disruption of the head posture mechanism, and aggravation of middle and inner ear conditions including dizziness, tinnitus, and eustachian tube blockage.

Orthodontists have long sought a device for realigning the mandible and maxilla. An early such device was the Herbst appliance, which is shown in German Patent No. 374,163. A metal band of the Herbst appliance was placed around an upper molar and a lower incisor tooth. These two bands were interconnected by a telescopic member to exert an anteriorly directed force on the lower jaw, which eventually brought the lower jaw into alignment with the upper jaw. The Herbst appliance, however, inhibited lateral movement of the jaw and it needed great strength to resist breakage from lateral jaw forces, therefore it was bulky and interfered with speaking, eating and other oral activities.

Similar telescopic devices include those shown in U.S. Pat. Nos. 3,618,214, 4,472,138, and 4,462,800, as well as French Patent No. 1,079,955. None of these dental appliances permitted lateral jaw movement, and they all required wires or braces to attach the device to a patient's teeth. Moreover, none of these devices were suitable for treating internally deranged temporomandibular joints in which the precise position of the mandible must be easily adjustable and must, in many cases, be able to be very gradually retruded from an extremely protruded position. Such gradual return to a more normal and comfortable jaw position is important, because any sudden retrusive shift can cause redisplacement of a recaptured displaced disc.

U.S. Pat. No. 4,382,783 did disclose a telescopic, intraoral orthodontic device which could be lengthened in very fine increments to realign the mandible and maxilla. This device, however, did not permit lateral jaw action and required placement of braces or bands on the teeth for attachment.

More recently, U.S. Pat. No. 4,618,324 disclosed a telescopic orthodontic device which was attached to upper and lower molars by a pair of opposing circular bands. The telescopic portion of the device was offset laterally from the teeth and towards the inner buccal surface to avoid interference with tooth movements. Pivotal connections between the bands and telescopic device also allowed transverse movement of the jaws without damaging the orthodontic appliance. In spite of these advantages, the appliance still placed excessive strain on the individual teeth to which it was attached, leading to tooth damage or fracture. Moreover, the lateral displacement of the device from the dental arches rubbed the inner buccal surfaces and was uncomfortable.

It is accordingly an object of the present invention to provide a comfortable intraoral orthopedic device for aligning the mandible and maxilla.

A further object of the invention is to provide an improved anchor for such a device.

Yet another object of the invention is to provide such a device which will minimize the risk of fracturing or otherwise damaging a user's teeth.

Yet another object is to provide a device which can be gradually and conveniently adjusted over fine increments of length to align the mandible and maxilla without redisplacement of the articular disc.

Another object is to provide such a device which permits lateral movement of the mandible for healthy function of the jaw muscles and performance of normal oral actions.

Yet another object of the invention is to provide such a device which allows such lateral movement and thereby prevents breakage of the appliance.

Finally, it is an object to provide an oral orthopedic appliance which can be easily fabricated in a dentist's office or laboratory for attachment either to the teeth or a pre-existing partial or full denture already worn by the patient.

SUMMARY OF THE INVENTION

The foregoing objects are achieved by a telescopic, intraoral orthopedic appliance which includes an extensible-contractable positioning member that extends between and alters the position of the mandible and maxilla relative to each other. The device is attached to the upper and lower dental arches by upper and lower channel-shaped attachment members which fit contiguously against a row of teeth in the maxilla and a row of teeth in the mandible. An anchor is embedded within each attachment member and protrudes outwardly from it to present a loop to which opposite ends of the positioning device are attached. The loop and positioning device are preferably contained in substantially the same plane, which also preferably includes at least a portion of the attachment member.

The positioning means includes a pair of hooks, one at each of its opposing ends, to engage the loops of the attachment member. The position of one of the hooks can be varied along the longitudinal axis of the appliance to adjust the length of the device. This adjustability feature allows gradual repositioning of the mandible without risking displacement of the articular disc, which is often caused by sudden jumps in the position of the mandible.

The anchor of the preferred embodiment is formed by twisting a wire loop to form loosely helically intertwined wire sections which are flattened to more closely fall into a plane. These wire sections are embedded in an attachment member with a loop projecting from the attachment member for receiving the positioning device. By making the attachment member of a liquid material such as acrylic, which flows between the intertwined sections, and then hardens, an extremely strong bond is established between the anchor and attachment member.

A better understanding of the invention can be had by reference to the following drawings and detailed description.

BRIEF DESCRIPTION OF THE DRAWINGS

FIG. 1 is a side elevational view of the appliance of the present invention in position on a user's teeth, portions of the appliance being broken away to reveal an anchor embedded in the appliance.

FIG. 2 is a cross sectional view taken along lines 2—2 of FIG. 1.

FIG. 3 is a front elevational view taken along lines 3—3 of FIG. 1.

FIG. 4 is a view of the appliance in FIG. 1, the mouth of the user having been opened to illustrate a malocclusion being corrected by the appliance.

FIG. 5 illustrates an alternative embodiment of an anchor in accordance with the present invention.

DETAILED DESCRIPTION OF A PREFERRED EMBODIMENT

The present invention is an orthopedic appliance for protruding the mandible. FIG. 4 illustrates retrusion of mandible 10 and the mandibular dental arch relative to maxilla 12 and the maxillary dental arch. Retrusion of the mandible 10 causes lower front tooth 10a to be set back from upper front tooth 12a by a distance L1, creating, an overjet. As shown in FIG. 3, appliances 14, 16 (see also FIG. 1 for appliance 14) of the present invention protrude mandible 10 such that teeth 10a, 12a are aligned when the mouth is closed. Remaining lower teeth 10b, 10c, 10d, 10e, 10f, 10g are also brought into their proper relationship with upper teeth 12b, 12c, 12d, 12e, 12f, 12g, 12h and 12i, respectively.

Appliances 14, 16 are mirror images of one another. Hence, only appliance 14 will be described in detail.

Appliance 14 includes an upper channel member 20 and a lower channel member 22. The upper channel member has a substantially U-shaped cross section (FIG. 2) which is bounded by an innér wall 24, outer wall 26 and transverse wall 28 which fit respectively contiguously against and fit tightly around the inner surface 30, outer surface 32 and apex 34 of the clinical crowns 36 of a series of adjacent teeth 12f, 12g and 12h. Similarly, lower channel member 22 has an inner wall 44, outer wall 46 and transverse wall 48 which respectively fit contiguously against and fit tightly around the inner surface 50, outer surface 52 and apex 54 of the clinical crowns 55 of a plurality of adjacent teeth 10d, 10e and 10f. The upper and lower channel members are preferably removable, but also can be fastened in place, as by cement, if desired. Each lower tooth 10 projects from an annular alveolar bone 56 which surrounds each lower tooth, while each upper tooth 12 projects from an annular alveolar bone 57 which surrounds each upper tooth. The clinical crown 36 of each upper tooth 12 is that portion of each upper tooth 12 which is covered by enamel and projects beyond alveolar bone 57. The lower clinical crown 55 of each lower tooth 10 is that portion of each lower tooth 10 which is covered by enamel and projects beyond alveolar bone 56.

The outer wall 26 of upper channel member 20 has a recessed lower portion 58 which is recessed from the exterior surface of wall 26 approximately a distance d (FIG. 2), which is the same distance as the diameter of a sleeve 80 of the extensible-contractable member described later. Recessed portion 58 presents an arcuate outer surface which extends between transverse wall 28 and outer wall 26, and is complementary in shape to a portion of the cylindrical sleeve 80 which fits in the recess along upper channel member 20.

The outer wall 46 of lower channel member 22 has a recessed upper portion 59 which is recessed from the exterior surface of wall 46 approximately a distance d, which is the same distance as the diameter of sleeve 80. Recessed portion 59 presents an arcuate outer surface which extends between transverse wall 48 and outer wall 46, and is complementary in shape to a portion of the cylindrical sleeve 80 which fits in the recess along the lower channel member 22.

An upper anchor 60 is embedded within outer wall 26 of upper channel member 20, and includes a pair of intertwined wires 62, 64 which are flattened into a generally vertical plane (FIG. 2) to occupy less space and minimize outward projection away from the teeth. Wires 62, 64 are embedded in wall 26. Preferably the upper channel member 20 comprises an attachment means formed of a liquid, such as acrylic, which hardens to embed the wires in place. Wires 62, 64 can thus be embedded by molding acrylic channel member 20 around the wires. The intertwined wires may be loosely helically twisted to provide small open loops through which the acrylic flows and sets to retain anchor 60 in the acrylic member 20. Wires 62, 64 are joined at a loop 66 which extends beyond a rear edge of wall 26. For strength and to prevent bending of the neck of the wires at the base of loop 66, the base of the loop is preferably embedded in the acrylic member 20. As best seen in FIG. 2, the loop 66 extends horizontally and posteriorly to upper channel member 20 above recessed portion 58. In the disclosed embodiment, only a small portion of loop 66 extends beyond the outer surface of wall 26.

A lower anchor 70 is embedded within outer wall 46 of lower channel member 22, and includes a pair of helically intertwined wires 72, 74 which are flattened into a generally vertical plane to occupy less space. Wires 72, 74 are also embedded in wall 46 such as by molding acrylic around the wires such that the acrylic flows through the loops formed by the intertwined wires to securely retain the anchor 70 when the acrylic sets. Wires 72, 74 are joined at a loop 76 that extends beyond the front edge of wall 46. Like loop 66, the base of loop 76 is preferably embedded in channel member 22. Loop 76 extends horizontally anteriorly of the front edge of channel member 22 adjacent outer wall 46. A small portion of loop 76 extends beyond the outer surface of wall 46.

An extensible-contractable positioning means extends between upper and lower channels 20, 22 to exert a protrusive force on mandible 10. This telescopic device includes a cylindrical tube or sleeve 80 of diameter d having a first internally threaded open end 82 and an open second end 84. A first hook 86 extends from end 82 and includes a hook portion 88 which hooks into and is closed around first loop 66, and an externally threaded shaft 90 which mates with the threads inside first end 82 of sleeve 80. The threads of shaft 90 are preferably at a slightly different pitch than the threads of sleeve 80 and the sleeve is slightly crimped. Consequently, the shaft 90 resists turning so that no lock nut is needed. Any such locking devices could irritate a patient's cheek. Other biasing or resistance mechanisms can also, of course, be used to counter unintentional adjustment of the shaft and sleeve during use by a patient. For example, either component may be bent slightly. The first hook 86 is substantially coplanar with a plane extending longitudinally through sleeve 80 and wall 26, and is preferably in a vertical plane as shown in the drawings.

A rod 92 projects through open end 84 into sleeve 80 and reciprocates telescopically within the sleeve. Rod 92 includes a second hook 94 which hooks into and is closed around lower loop 76. Second hook 94 is preferably coplanar with a plane extending longitudinally through rod 92 and wall 46, the plane preferably being vertical as shown in the drawings.

As seen best in FIG. 2, appliance 16 does not extend laterally away from channel members 20, 22 but instead fits against their outer surfaces to diminish interference with oral activities and reduce damage to the mucosa of the inner buccal surface. The recesses 58, 59 cooperatively provide an indentation in walls 26, 46 in which appliance 16 fits when the mouth is closed, as shown in FIG. 2. Even when the mouth is open, as shown in FIG. 4, the appliance remains in substantially the same plane coincident with walls 26, 46. Some movement out of this plane is desirable, however, to permit lateral movement of the jaw and prevent damage to the appliance. Such lateral movement is allowed by the pivotal connections between loop 66 and hook 88 of the upper channel member, and loop 76 and hook 94 of the lower channel member.

FIG. 4 illustrates the relative position of the appliance when the mouth is fully open. A portion of rod 92 of length L2 projects out of open end 84 of sleeve 80. The distance L2 is measured from the beginning of the bent portion of hook 94 to the open end 84 of sleeve 80, and is approximately the same as the distance L1 of the overbite being corrected. As the mouth closes, rod 92 slides into sleeve 80 until hook 94 abuts end 84 to halt the inward movement of rod 92 and exert a protruding force on mandible 10 to hold it forward a distance L2 while the mouth remains closed.

Mandible 10 can be progressively protruded or allowed to retrude in small increments by slightly rotating sleeve 80 in a direction that moves threaded shaft 90 in or out of sleeve 80. As sleeve 80 rotates, the internal threads of sleeve 80 and external threads on shaft 90 force shaft 90 in or out of sleeve 80 to shorten or lengthen appliances 14, 16 and alter the protrusive force on mandible 10. This simple adjustment in the length of appliance 16 can be performed during an office visit by a dentist or by a patient at home. The appliances can be adjusted in this manner without removing them from the mouth, which avoids the problem of redisplacement of the articular disc once the protrusive force is removed.

Appliances 14, 16 are simple to manufacture in a laboratory or dentist's office, and are easy to install. Also, the appliance is designed so that it may be easily attached to partial or full dentures which are already being worn by the patient to replace missing teeth.

An alternate embodiment of the anchor 60 is shown in FIG. 5. This anchor 100 includes a flattened metal bar or cylinder 102 with an outer surface which is made irregular by a plurality of protuberances 104 which project outwardly from bar 102. A series of cylindrical holes 106 extend through the body of bar 102 to provide passageways through which acrylic or other moldable material flows to attach the bar to a channel member adjacent to anchor 100. A loop 108 is either welded to or molded integral with bar 102 for extending out of the channel member and attaching to hooks 86, 94 of the telescopic appliance.

Having illustrated and described the principles of my invention with reference to one preferred embodiment, it should be apparent to those persons skilled in the art that such invention may be modified in arrangement and detail without departing from such principles. I claim as my invention all such modifications as come within the true spirit and scope of the following claims.

I claim:

1. A telescopic, intraoral orthopedic appliance for aligning the mandible and maxilla, comprising:
   upper attachment means for attaching said appliance to said mandible and lower attachment means for attaching said appliance to said maxilla;
   upper anchor means embedded within and extending out of said upper attachment means and lower anchor means embedded within and extending out of said lower attachment means;
   a sleeve having a first end and an open second end;
   a first hook means carried by said first end for attachment to one of said anchor means, said first hook means being substantially coplanar with a plane extending longitudinally through said sleeve; and
   a rod projecting through said open end for reciprocating telescopic movement within said sleeve, said rod including a second planar hook means which is coplanar with a plane extending longitudinally through said rod.

2. The appliance of claim 1 wherein said upper anchor means includes an upper loop and said lower anchor means includes a lower loop, and said first and second hook means each interengage one of said upper or lower loops.

3. A telescopic, intraoral orthopedic appliance for aligning the mandible and maxilla, comprising:
   upper attachment means for attaching said appliance to said mandible and lower attachment means for attaching said appliance to said maxilla;
   upper anchor means embedded within and extending out of said upper attachment means and lower anchor means embedded within and extending out of said lower attachment means;
   a sleeve having a first end and an open second end;
   a first hook means carried by said first end for attachment to one of said anchor means, and first hook means being substantially coplanar with a plane extending longitudinally through said sleeve;
   a rod projecting through said open end for reciprocating telescopic movement within said sleeve, said rod including a second hook means; and
   wherein said first end of said sleeve is open and internally threaded, and said first hook means comprises a hook portion and an externally threaded shaft which mates in threaded engagement with said internally threaded first end of said sleeve.

4. The appliance of claim 3 in which at least one of said sleeve and said shaft includes means for resisting relative turning of said sleeve and shaft.

5. The appliance of claim 3 wherein said first hook means is substantially planar and coplanar with a plane extending longitudinally through said sleeve and said second hook means being coplanar with a plane extending longitudinally through said rod.

6. A telescopic, intraoral orthopedic appliance for aligning the mandible and maxilla, comprising:
   upper attachment means for attaching said appliance to said mandible and lower attachment means for attaching said appliance to said maxilla;
   upper anchor means embedded within and extending out of said upper attachment means and lower anchor means embedded within and extending out of said lower attachment means;

a sleeve having a first end and an upper end and having the first end coupled to one of the upper and lower attachment means; and wherein each said attachment means comprises a channel means having a substantially U-shaped cross section for fitting contiguously over the apex and inward and outward facing surfaces of the clinical crowns of a plurality of adjacent teeth.

7. A telescopic, intraoral orthopedic appliance for aligning the mandible and maxilla, comprising:

upper attachment means for attaching said appliance to said mandible and lower attachment means for attaching said appliance to said maxilla;

upper anchor means embedded within and extending out of said upper attachment means and lower anchor means embedded within and extending out of said lower attachment means;

a sleeve having a first end and an open second end and having the first end coupled to one of the upper and lower attachment means;

a rod having first and second ends, the first end of the rod projecting through said open end for reciprocating telescopic movement within said sleeve, the second end of said rod being coupled to the other of the upper and lower attachment means; and wherein each said anchor means has an outer surface which is irregular for retention within said upper and lower attachment means.

8. The appliance of claim 7 wherein said anchor means includes an intertwined pair of wires embedded within each of said upper and lower attachment means.

9. The appliance of claim 7 wherein said intertwined pair of wires of said upper anchor means forms an upper loop protruding out of said upper attachment means and said intertwined pair of wires of said lower anchor means forms a lower loop protruding out of said lower attachment means, a first hook at the first end of the sleeve and a second hook at the second end of the rod and said first and second hooks each interengage one of said upper or lower loops.

10. The appliance of claim 9 in which a portion of the upper loop is embedded in the upper attachment means and in which a portion of the lower loop is embedded in the lower attachment means.

11. The appliance of claim 9 wherein said upper loop is positioned outwardly of said teeth but substantially coplanar with at least a portion of said upper attachment means, and said lower loop is positioned outwardly of said teeth but substantially coplanar with at least a portion of said lower attachment means.

12. The appliance of claim 11 wherein said attachment means includes an outside wall for fitting contiguously against said outward facing sides of said teeth, and said anchor means is embedded in said outside wall.

13. The appliance of claim 8 wherein each said pair of wires are flattened substantially into a plane parallel to the outward facing surfaces of the adjacent teeth.

14. The appliance of claim 13 wherein each said pair of wires is loosely helically intertwined to provide spaces between the intertwined wires.

15. A telescopic, intraoral orthopedic appliance for aligning the mandible and maxilla, comprising:

upper attachment means for attaching said appliance to said mandible and lower attachment means for attaching said appliance to said maxilla;

upper anchor means embedded within and extending out of said upper attachment means and lower anchor means embedded within and extending out of said lower attachment means;

a sleeve having a first end and an open second end and having the first end coupled to one of the upper and lower attachment means;

a first hook means carried by said first end for attachment to one of said anchor means;

a rod having first and second ends, the first end of the rod projecting through said open end for reciprocating telescopic movement within said sleeve, the second end of said rod being coupled to the other of the upper and lower attachment means; and wherein each said anchor means includes a metal member through which a plurality of openings extend.

16. The appliance of claim 15 wherein said metal member further includes a plurality of protuberances projecting outwardly from the surface of said metal member.

17. A telescopic orthopedic appliance for aligning the mandible and maxilla, comprising:

upper and lower channel members each having a substantially U-shaped cross section and including inner, outer and transverse walls for respectively fitting contiguously against the inner surface, outer surface and apex of the clinical crowns of a plurality of adjacent teeth;

an upper anchor means embedded within said upper channel and a lower anchor means embedded within said lower channel, each said upper anchor means including a pair of helically intertwined wires extending through said outer wall of said upper channel member, said lower anchor means including a pair of helically intertwined wires extending through said outer wall of said lower channel member, the wires of said upper anchor means forming an upper loop protruding from said upper attachment means outwardly of said outer surface of said teeth, the wires of said lower anchor means forming a lower loop protruding from said lower attachment means outwardly of said outer surface of said teeth;

a sleeve having a first internally threaded open end and an open second end;

a first hook means comprising a hook portion interengaging said first loop, and an externally threaded shaft which mates with said internally threaded first end of said sleeve; and a rod projecting through said open second end for reciprocating telescoping movement within said sleeve, said rod including a second hook means which interengages said lower loop.

18. The appliance of claim 17 in which the helically intertwined wires of the upper and lower anchor means are each flattened.

19. The appliance of claim 17 in which said first hook means is coplanar with a plane that extends longitudinally through said shaft and in which said second hook means is coplanar with a plane extending longitudinally through said shaft.

20. A telescopic, intraoral orthopedic appliance for aligning the mandible and maxilla, comprising:

extensible-contractable positioning means for extending between and altering the position of said mandible and maxilla relative to one another;

an upper attachment means for attaching said positioning means to said maxilla, comprising a member molded to fit contiguously against a plurality of teeth of said maxilla;

a lower attachment means for attaching said positioning means to said mandible, comprising a member molded to fit contiguously against a plurality of teeth of said mandible;

an upper anchor means embedded within and protruding outwardly from said upper attachment means for anchoring a first end of said positioning means to said upper attachment means; and a lower anchor means embedded within and protruding outwardly from said lower attachment means for anchoring a second end of said positioning means to said lower attachment means.

21. The appliance of claim 20 wherein said upper anchor means includes a loop protruding out of said upper attachment means and interengaging said first end of said positioning means, and said lower anchor means includes a loop protruding out of said lower attachment means and interengaging said second end of said positioning means.

22. The appliance of claim 21 further comprising a hook means at each of said first and second ends of said positioning means for interengaging said loops protruding from said upper and lower attachment means, the hook means being coplanar.

23. The appliance of claim 22 further comprising adjustment means for selectively varying the position of one of said hook means along the longitudinal axis of said appliance.

24. An anchor according to claim 23 in which a portion of the loop is embedded in the attachment means.

25. The appliance of claim 20 further comprising adjustment means for selectively changing the position of one of said positioning means along the longitudinal axis of the appliance and means for biasing the adjustment means against unintentional adjustment during use.

26. An anchor for anchoring an intraoral orthodontic or orthopedic appliance to a user's teeth, the anchor comprising:

an attachment means for connection to plural teeth at one side of the user's maxilla or mandible; and a wire twisted to form a loop at one end and intertwined wire sections at the opposite end, the intertwined wire sections being embedded in the attachment means.

27. An anchor according to claim 26 in which the intertwined wire sections are loosely twisted to provide openings between such intertwined wire sections, the attachment means being formed of a liquid which flows through the opening and hardens to embed the intertwined wire sections.

28. An anchor according to claim 26 in which the intertwined wire sections are flattened.

29. An anchor according to claim 26 in which the intertwined wire sections are loosely twisted to provide openings between such intertwined wire sections, the attachment means being formed of a liquid which flows through the opening and hardens to embed the intertwined wire sections, the intertwined wire sections also being flattened, and a portion of the loop being embedded in the attachment means.

30. An intraoral orthodontic or orthopedic appliance anchor for connection to an attachment member, the attachment member being of the type which is to be placed in a user's mouth and attached to a user's teeth, the anchor comprising:

an elongated retention means for embedding into and retention within the attachment member, said retention means having an irregular outer surface; and loop means connected to said retention means for projecting from the attachment member when the retention means is embedded in the attachment member.

31. The anchor of claim 30 wherein said retention means is a wire twisted to form intertwined wire sections.

32. The anchor of claim 30 wherein said wire further forms said loop means.

33. The anchor of claim 32 wherein said wire is loosely twisted to provide openings between said intertwined wires.

34. The anchor of claim 32 wherein said intertwined wire sections are flattened substantially into a plane.

35. The anchor of claim 30 wherein said retention means includes a metal bar.

36. The anchor of claim 35 wherein said metal bar defines a plurality of holes projecting through said bar.

37. The anchor of claim 36 wherein said metal bar further includes a plurality of protuberances projecting outwardly from the surface of said bar.

* * * * *